United States Patent
Satzinger et al.

(10) Patent No.: US 10,161,525 B2
(45) Date of Patent: Dec. 25, 2018

(54) SEALING SYSTEM AND METHOD FOR THE PRODUCTION THEREOF

(71) Applicant: DIONEX SOFTRON GMBH, Germering (DE)

(72) Inventors: Adolf Satzinger, Olching (DE); Thomas Armin Alexander Eichhorn, Munich (DE)

(73) Assignee: DIONEX SOFTRON GMBH, Germering (DE)

( * ) Notice: Subject to any disclaimer, the term of this patent is extended or adjusted under 35 U.S.C. 154(b) by 267 days.

(21) Appl. No.: 14/802,067

(22) Filed: Jul. 17, 2015

(65) Prior Publication Data

US 2016/0018001 A1 Jan. 21, 2016

(30) Foreign Application Priority Data

Jul. 17, 2014 (DE) .................. 10 2014 110 077

(51) Int. Cl.
| | | |
|---|---|---|
| *F16J 15/18* | (2006.01) | |
| *F16J 15/32* | (2016.01) | |
| *F16J 15/56* | (2006.01) | |
| *G01N 30/60* | (2006.01) | |
| *F04B 53/16* | (2006.01) | |
| *F16J 15/3276* | (2016.01) | |
| *F16J 15/3268* | (2016.01) | |

(52) U.S. Cl.
CPC ............ *F16J 15/18* (2013.01); *F04B 53/164* (2013.01); *G01N 30/6026* (2013.01); *F16J 15/3268* (2013.01); *F16J 15/3276* (2013.01); *F16J 15/56* (2013.01); *G01N 30/6034* (2013.01)

(58) Field of Classification Search
CPC ............... G01N 30/6026; F04B 53/164; F16J 15/3268; F16J 15/3276; F16J 15/56
See application file for complete search history.

(56) References Cited

U.S. PATENT DOCUMENTS

| | | | | |
|---|---|---|---|---|
| 2,625,414 | A * | 1/1953 | Kranz | F16J 15/28 |
| | | | | 277/346 |
| 7,568,424 | B2 * | 8/2009 | Hopkins | F04B 53/02 |
| | | | | 417/415 |
| 8,806,922 | B2 | 8/2014 | Hochgraeber | |
| 2008/0019851 | A1 * | 1/2008 | Hopkins | F04B 53/02 |
| | | | | 417/415 |
| 2008/0083324 | A1 | 4/2008 | Ackermann et al. | |
| 2008/0236107 | A1 * | 10/2008 | Mastrogiacomo | B30B 11/002 |
| | | | | 53/485 |

(Continued)

FOREIGN PATENT DOCUMENTS

| | | |
|---|---|---|
| DE | 4225556 A1 | 2/1994 |
| DE | 19615157 A1 | 10/1997 |

(Continued)

OTHER PUBLICATIONS

DE-102008041503-A1 Machine Translation from: worldwide.espacenet.com; retreived Aug. 25, 2017.*

*Primary Examiner* — Nicholas L Foster

(57) ABSTRACT

The invention relates to a seal for high pressure applications, in which a static and a dynamic sealing portion are separated from each other by a material thin point in such a manner that plastic flowing through the thin point is suppressed even if one of the two sealing portions is acted upon under high pressure as far as elastic compression.

19 Claims, 3 Drawing Sheets

(56) References Cited

U.S. PATENT DOCUMENTS

| | | | |
|---|---|---|---|
| 2009/0028479 A1 | 1/2009 | Dittmann | |
| 2010/0000927 A1* | 1/2010 | Beigel | B29C 43/18 |
| | | | 210/198.2 |
| 2010/0288025 A1 | 11/2010 | Hochgraeber | |
| 2013/0323103 A1* | 12/2013 | Shreve | F04B 1/0448 |
| | | | 417/437 |
| 2014/0070530 A1* | 3/2014 | Haeckel | F16L 21/045 |
| | | | 285/346 |
| 2014/0338431 A1 | 11/2014 | Hochgraeber | |
| 2014/0345371 A1 | 11/2014 | Hochgraeber | |

FOREIGN PATENT DOCUMENTS

| | | | | |
|---|---|---|---|---|
| DE | 102006012057 A1 | 9/2007 | | |
| DE | 102007007273 A1 | 4/2008 | | |
| DE | 102008041503 A1 * | 4/2009 | ............ | F04B 53/143 |
| DE | 102008006266 | 8/2009 | | |
| EP | 0894213 B1 | 9/2001 | | |
| EP | 1701071 A1 | 9/2006 | | |

* cited by examiner

SEALING SYSTEM AND METHOD FOR THE PRODUCTION THEREOF

CROSS REFERENCE TO RELATED APPLICATIONS

This application claims the priority benefit under 35 U.S.C. § 119 to German Patent Application No. 10 2014 110 077.8, by Adolf Satzinger and Thomas Armin Alexander Eichhorn for "Sealing system and method for the production thereof" filed on Jul. 17, 2014, the disclosure of which is incorporated herein by reference.

FIELD OF THE INVENTION

The present invention relates to a sealing system for high pressure applications.

BACKGROUND

In high performance liquid chromatography (HPLC), piston pumps are customarily used for conveying liquids. The piston can be formed here from a smooth rod manufactured within highly exacting tolerances, for example made from zirconium oxide or sapphire. Said rod moves relative to a stationary seal, past which the rod slides with as little friction as possible. The seal is intended to close the gap between a pump head forming the cylinder and the piston oscillating therein. There are two functional sealing regions in this case: firstly between the positionally fixed seal and the moving piston and secondly between the positionally fixed seal and the likewise positionally fixed pump head.

There are also very similar conditions in HPLC metering syringes which provide a precisely defined quantity of the medium to be analyzed. If the stroke space of the metering syringe is joined into the conveying path of the high pressure pump, the stroke space of the syringe correspondingly also has to be readily sealed at the plunger in order to permit the high operating pressures of frequently more than 1500 bar. For high pressure pumps or metering syringes in HPLC technology, there are therefore comparable requirements with regard to the sealing.

For metering syringes, the axial movability of known seals has proven problematic. The reciprocating movement of the piston leads to migration of the seal at only slightly increased operating pressures. Since metering syringes specifically depend on a very precise determination of the volume received, even only a slight displacement of the seal makes it difficult to reproduce the sample quantities to be received.

Furthermore, there is the problem that the known seals have to resolve dynamic and static sealing tasks, for which, however, different material properties are generally required. Therefore, known high pressure seals are customarily composed of thermoplastic material with good sliding properties, but low rigidity. For high pressure applications, seals having sealing lips which also utilize the system pressure for sealing purposes are known. The sealing lips which are spaced apart by a recess bear here radially on the inside against the shaft to be sealed or the piston rod, while the outer sealing lip, which is connected integrally to the inner sealing lip, bears against the housing. The cavity formed between the sealing lips is subjected to system pressure in order to push the inner sealing lip radially inward for an improved sealing action (hydraulic seal). Since, however, such a seal does not function adequately for operating pressures only just above ambient pressure, the seals are frequently prestressed.

However, the dynamically stressed sealing lip has to have sliding properties which are as good as possible, but such a material is frequently too flexible to be inherently prestressed. A metallic spring element is therefore frequently inserted into the cavity of the seal in order thereby to push the sealing lips radially apart against the housing or the piston rod or shaft. However, in HPLC technology, metals along the conveying path of the sample are undesirable because of possible chemical reactions with the sample. In addition, the cavity for the metallic prestressing element is a dead space which is difficult to flush through and in which residues or air bubbles may accumulate, which should be avoided. In general, in HPLC technology, there is a trend toward reducing the flow-through volume and toward metal-free paths for a biocompatible application. However, even non-metallic prestressing elements, for example O rings, are generally not chemically inert to all of the substances to be expected in the medium. They may be attacked and destroyed by said substances such that the sealing action is no longer provided.

For the pure static sealing, good sliding properties of the sealing material are not required since the components to be sealed in relation to one another do not carry out any relative movement. The integral seals previously known from the prior art do not meet these different requirements regarding the sealing properties.

SUMMARY

It is therefore the object of the invention to provide a sealing mechanism and a method for installing same, with which the requirements regarding static and dynamic sealing portions can be met uniformly well. At the same time, the intention is for the sealing mechanism to provide a sufficiently high degree of stability and positional security. Bio inert properties and the avoidance of dead spaces are also desirable.

The invention is based on the finding that the requirements of a dynamic seal should be considered separately from those regarding a static seal. The purely statically stressed portion of a seal can be manufactured from a high-strength plastics part, such as, for example, PEEK. In order to obtain a static sealing action, the corresponding sealing portion can be deformed plastically under high pressure in order to fill the entire space available thereto and to be placed tightly against the gaps to be sealed. Under pressurizing further, the sealing portion can be elastically compressed and thus maintains a particularly good sealing action. By contrast, the dynamically acting sealing portion does not require any plastic deformation; instead, said sealing portion can be preshaped in such a manner that, in the mounted state, said sealing portion is pressed with a prestress against the component to be dynamically sealed (here: piston rod) in order to obtain an adequate sealing action even at low system pressures. A high-strength plastic, such as PEEK, is also suitable for this sealing portion, with a sliding element which bears directly against the piston rod, being used. Despite their different sealing function, the two sealing portions can be designed as an integrally formed seal, wherein the two sealing portions are exposed to different loadings during installation and during operation. According to the invention, said sealing portions are substantially separated from each other spatially, with a continuous sealing surface extending from the piston rod to the end of an only statically stressed sealing gap between the seal and the housing.

The sealing system according to the invention is provided for high pressure applications, in particular in HPLC technology. A housing, in particular a pump head, having a pressurizable stroke space is intended to be sealed here in relation to a movable piston rod, which is formed about an axis. The sealing system here comprises a seal with a first, dynamic sealing portion for sealing between the seal and the piston rod. A second, static sealing portion is provided for sealing between the seal and the housing. The two sealing portions are formed integrally with each other.

According to the invention, the first sealing portion merges via a material thin point, which is produced by plastic deformation, into the second sealing portion. The material thin point is designed in such a manner that the sealing material of the second sealing portion cannot flow even under high pressure through the thin point in the direction of the first sealing portion.

This gives rise to the advantage that the second sealing portion is pressable with a press-on force into the sealing seat provided for said portion, the press-on force being substantially independent of the press-on force which acts on the first sealing portion. In other words: under suitable geometric and physical boundary conditions, the second sealing portion can be subjected to a particularly high pressure which, in addition to a preliminary plastic deformation, leads to an elastic compression of the second sealing portion. However, the thin point connecting the two sealing portions prevents the material of the second sealing portion from flowing under said pressurization through the thin point to the first sealing portion. The pressure introduced into the second sealing portion therefore cannot dissipate due to flowing of the material and is instead permanently maintained in the second sealing portion.

The seat into which the seal is inserted on the housing or pump head is preferably coordinated with the dimensions of the first sealing portion in such a manner that a pressurization of the first sealing portion within the context of installing the seal does not lead to the elastic compression thereof. Instead, the first sealing portion can yield to the pressurization thereof by means of plastic deformation or displacement without building up an internal pressure comparable to the second sealing portion. Although the seal is advantageously constructed as a single piece, the individual sealing portions provided for static or dynamic sealing purposes therefore— unlike in the prior art—can be pressurized or deformed differently in a specific manner.

According to an advantageous embodiment of the invention, the second sealing portion is surroundable on all sides, with the exception of the thin point, by the housing or press-on elements which are separate therefrom, in order to build up a predeterminable pressure in said sealing portion. Such a sealing portion, for example manufactured from PEEK, will be plastically deformed under sufficiently high pressurization and, in the process, will penetrate in the best possible manner into existing sealing gaps and reliably close same. In order to prevent an unintentional yielding of the material, the components bounding the second sealing portion can be arranged or fitted as closely spaced apart from one another as possible. The thin point which then produces the single material connection of the second sealing portion to the first sealing portion can also be dimensioned to be sufficiently tight in order to prevent the possible flowing of the sealing material.

The material thin point expediently has a thickness of less than 0.5 mm. A thickness of less than 0.1 mm is particularly preferred. At maximum, the thickness is preferably less than 0.05 mm, as a result of which a possible material flow is particularly reliably suppressed. In this case, "thickness" should be understood as meaning the smallest distance between two opposite boundary lines in the cross section of the thin point, and therefore an increase in said distance would facilitate a material flow through the thin point.

The material thin point is expediently designed as a ring which is rectangular in cross section and encircles the axis X of the piston rod (the X axis here lies in the imaginary cross-sectional plane). The long sides of the rectangular cross section can extend parallel to the X axis, and therefore the material connection extends from the second to the first sealing portion in a manner parallel to the X axis. However, in a particularly preferred embodiment, the long sides of the rectangular cross section extend perpendicularly to the X axis, and the material connection between the two sealing portions thus runs in the radial direction with respect to the X axis. In this case, the thin point can be produced particularly simply by axial action upon the seal, as is also described below.

According to an advantageous embodiment of the invention, in the fitted state, the first sealing portion extends substantially parallel to the X axis. On the outer side thereof facing away from the piston rod, a pressure volume which is connected to the stroke space and is in the shape of an annular gap is provided in order to be able to press the first sealing portion radially inward against the piston rod at the pressure prevailing in the stroke space. Such a hydraulic seal supports the same sealing action of the first sealing portion, the latter already producing the sealing action because of a prestress, which is introduced during the installation, in relation to the piston rod. A channel supplementing the pressure volume and encircling the first sealing portion on the outer side in a spiral manner ensures a uniform flow profile and the discharging of air bubbles in the event that medium is intended to be conveyed along the annular pressure volume to or away from the stroke space.

The method for installing the sealing system according to the invention first of all comprises the arrangement of the seal in a sealing seat which is formed in the housing or pump head. The seal is subsequently pressed into the sealing seat, which can take place, for example, by a press-on element being screwed into the pump head, the press-on element subjecting the initially still undeformed seal to a press-on force in the axial direction. The preferably rotationally symmetrical press-on element here has, on the end side thereof facing the seal, a press-on profile with an annular projection which, as the screwing-in operation continues, is pressed into the seal and displaces the sealing material in this region radially in a plastic or elastic manner until a material thin point having the preferred dimensions mentioned above has been produced. The radially inwardly pushed sealing material is then supplied to the first sealing portion while the radially outwardly pushed material is pressed into the second sealing portion.

At the same time as the formation of the thin point, the second sealing portion, according to a preferred embodiment of the method, is prestressed to such an extent that said sealing portion completely fills, by means of plastic flowing, the space available thereto. At the same time, the thin point, as already explained, is dimensioned in such a manner that a material flow in the direction of the first sealing portion is suppressed. The material of the second sealing portion "blocked" in this manner is thereby pressed with a large force tightly against the sealing seat or the housing and is compressed or prestressed elastically, as a result of which a particularly good sealing action can be obtained.

The first sealing portion can also be pressurized when the seal is braced by means of the press-on element, said sealing portion being able to yield to the pressure by being deformed into a space predetermined therefor in the sealing seat, and therefore complete elastic compression of said first sealing portion does not take place. Depending on the structural configuration of the sealing seat and of the first sealing portion, the deformation can also be used in order to generate an additional radial press-on force on the piston rod by the first sealing portion. While the second (static) sealing portion is pressed under high pressure against the wall surrounding it in order to produce a sealing action, the first sealing portion achieves the sealing action thereof firstly by means of a prestress which arises by means of the radial expansion thereof during the installation on the piston rod. For this purpose, the first sealing portion can be manufactured, for example, conically or cylindrically with an undersize in relation to the piston. Additional sealing action is produced by pressurization on the outer side of the first sealing portion by the medium present under high pressure in the stroke space.

Although the material thin point is expediently produced during the installation of the seal, said material thin point can basically also already be provided previously on the seal. The seal is then already divided prior to the installation into the first and the second sealing portions separated via the thin point. When such a seal is clamped in position, the thin point is then "merely" stabilized in its already existing shape by pressurization via a press-on element without a significant displacement of material out of the region of the thin point taking place. However, the pressurization of the second sealing portion as far as the elastic compression can nevertheless take place and the material flow through the thin point is also prevented in a customary manner.

Furthermore, it is conceivable to stabilize the previously produced thin point in the shape thereof during the installation by means of adjacent rigid housing portions or auxiliary elements without said thin point having to be actively pressurized by means of a press-on element.

Since, despite the high sealing action sought, the seal is intended to act with as small frictional force as possible upon the piston moving relative thereto, in a further embodiment of the invention, the first sealing portion is provided on the inner side thereof facing the piston rod with a sliding element which may have more favorable sliding properties than the material of the first sealing portion. Depending on the radial wall thickness of said sliding element, the latter can be provided with a prestress which acts in the radial direction and can produce a certain dynamic sealing action even without external pressurization.

An integral seal made from a material having sliding properties which are improved in relation to PEEK (for example, a PTFE compound) which, however, has sufficient rigidity for radially prestressing the first sealing portion is also conceivable. In this case, the separate sliding element on the inner side of the first sealing portion can also be omitted, and therefore said sealing portion acts directly on the piston rod.

By means of the integral design of the seal and the fixed clamping of the second sealing portion into position, it is ensured that the seal reliably retains the axial position thereof. The sliding element can also be secured in the axial position thereof by the first sealing portion engaging axially around the sliding element, for example by means of radial projections. Alternatively, when the seal is pressed into position, a portion of the sliding element can also be pressed into a region of the first sealing portion, and therefore a form-fitting connection is produced in the axial direction between first sealing portion and sliding element.

The sealing system according to the invention can advantageously be produced from or with bio-inert materials, which include, in particular, PEEK or PTFE.

Although the abovementioned sealing system is suitable in particular for piston-cylinder seals, said sealing system is not limited thereto. Since the sought sealing action is basically achieved independently of a relative movement of the piston in relation to the seal, the seal can also be used for purely static sealing tasks. Instead of a piston moving in a reciprocating manner, the seal described can also be used for sealing a rotating shaft.

The sealing system according to the invention has been explained with reference to a piston rod which is movable in a reciprocating manner in the stroke space and along which sealing is intended to be achieved. However, the sealing system is also suitable for other applications, such as, for example, for shaft seals, and therefore, for a piston rod moving in a reciprocating manner and a shaft moving in a rotating manner, reference can be made within the extended sense to a "rod" in both cases. With regard to a shaft seal, "stroke space" within the meaning of this invention is therefore also intended to comprise a pressurizable space having an invariable volume.

BRIEF DESCRIPTION OF THE DRAWINGS

An embodiment of the invention will be explained in more detail below with reference to an example in the Figures.

DETAILED DESCRIPTION OF EMBODIMENTS

Figure 1:
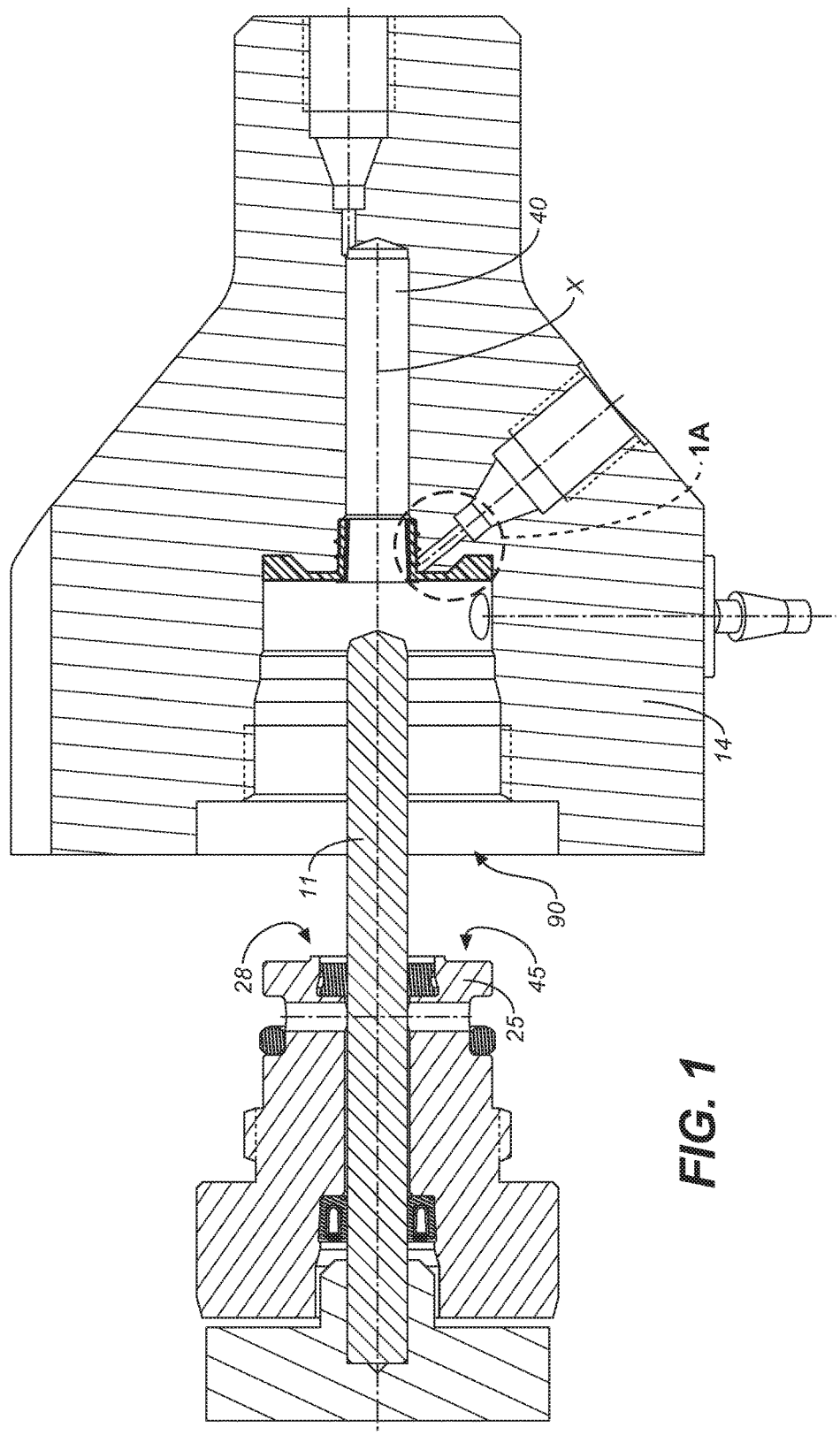
FIG. 1 shows a pump head prior to the installation with a seal inserted therein.

FIG. 1 shows, in a sectional illustration, a housing 14 which is designed as a pump head and is formed in a substantially rotationally symmetrical manner about an axis X. Within the context of the installation, a piston rod 11 is intended to be pushed centrally along the X axis into a stroke space 40 of the housing and, in the process, to be sealed by a sealing system according to the invention.

Figure 1A:
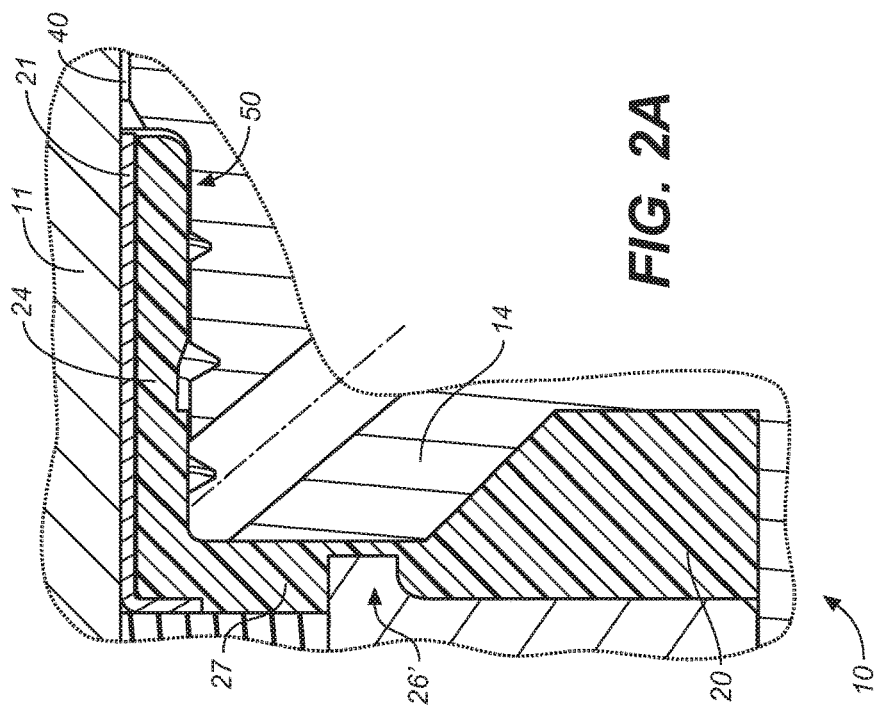
FIG. 1A is an enlarged detail thereof.

In the enlarged illustration of the detail shown in FIG. 1A, the sealing system 10 is illustrated prior to the installation of the piston rod 11. Said sealing system includes a seal 30 which has a first sealing portion 24 which extends substantially parallel to the axis X and is intended to act upon the piston rod 11 (to be introduced later) inwardly in the radial direction. The sealing portion 24 can therefore also be referred to as a dynamic sealing portion.

The seal 30 furthermore comprises a second sealing portion 20 which is connected integrally to the sealing portion 24. The sealing portion 20 is connected to the first sealing portion 24 via a material region 26 extending radially away from the axis X. The second sealing portion 20 serves for static sealing and can therefore also be referred to as a static sealing portion. The seal 30 formed from the first and second sealing portions 24, 20 serves to seal the pressurized stroke space 40 in relation to the piston rod 11 and the rear region 90 of the pump head 14. The intention here is to provide a seal along the piston rod 11 by the dynamic sealing portion 24 while the static sealing portion 20 is intended to ensure sealing along the sealing seat 22 in the housing 14.

On the inner side thereof facing the axis X, the first sealing portion 24 is provided with a sliding element 21 which has particularly good sliding properties and therefore permits the relative movement of the piston rod 11 in relation to the seal in a manner as free from friction as possible. Before the installation of the piston rod 11, the sealing element 21 is of slightly conical or cylindrical design with an undersize, and therefore the smallest diameter thereof is smaller than that of the piston rod 11. The first sealing portion 24 also has, along the X axis, a tapered portion which is intended to serve for producing a prestressing force during the installation of the piston.

Figure 2A:
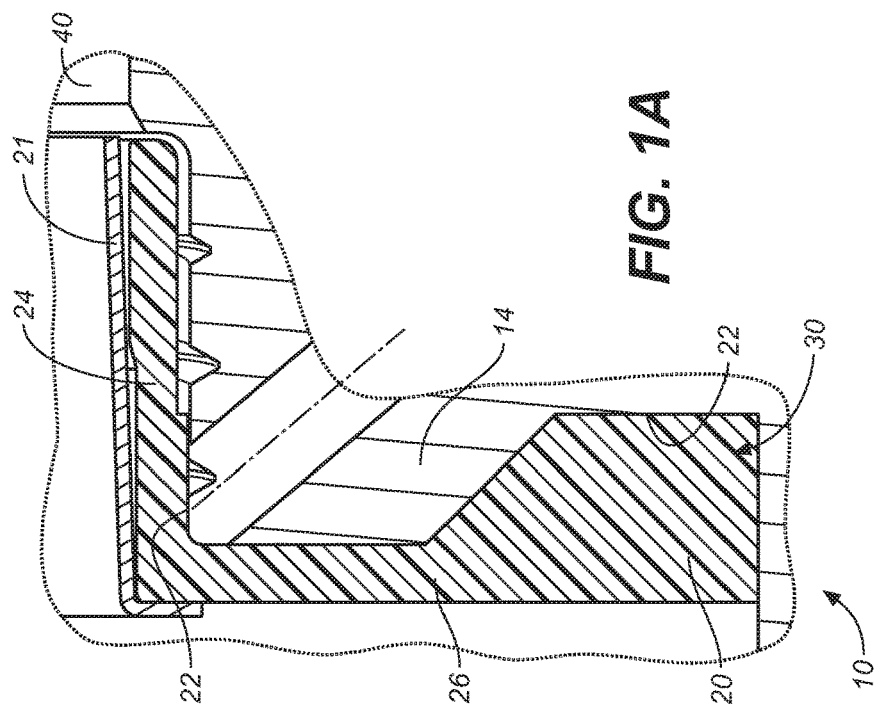
FIG. 2A is an enlarged detail thereof.
Figure 2:
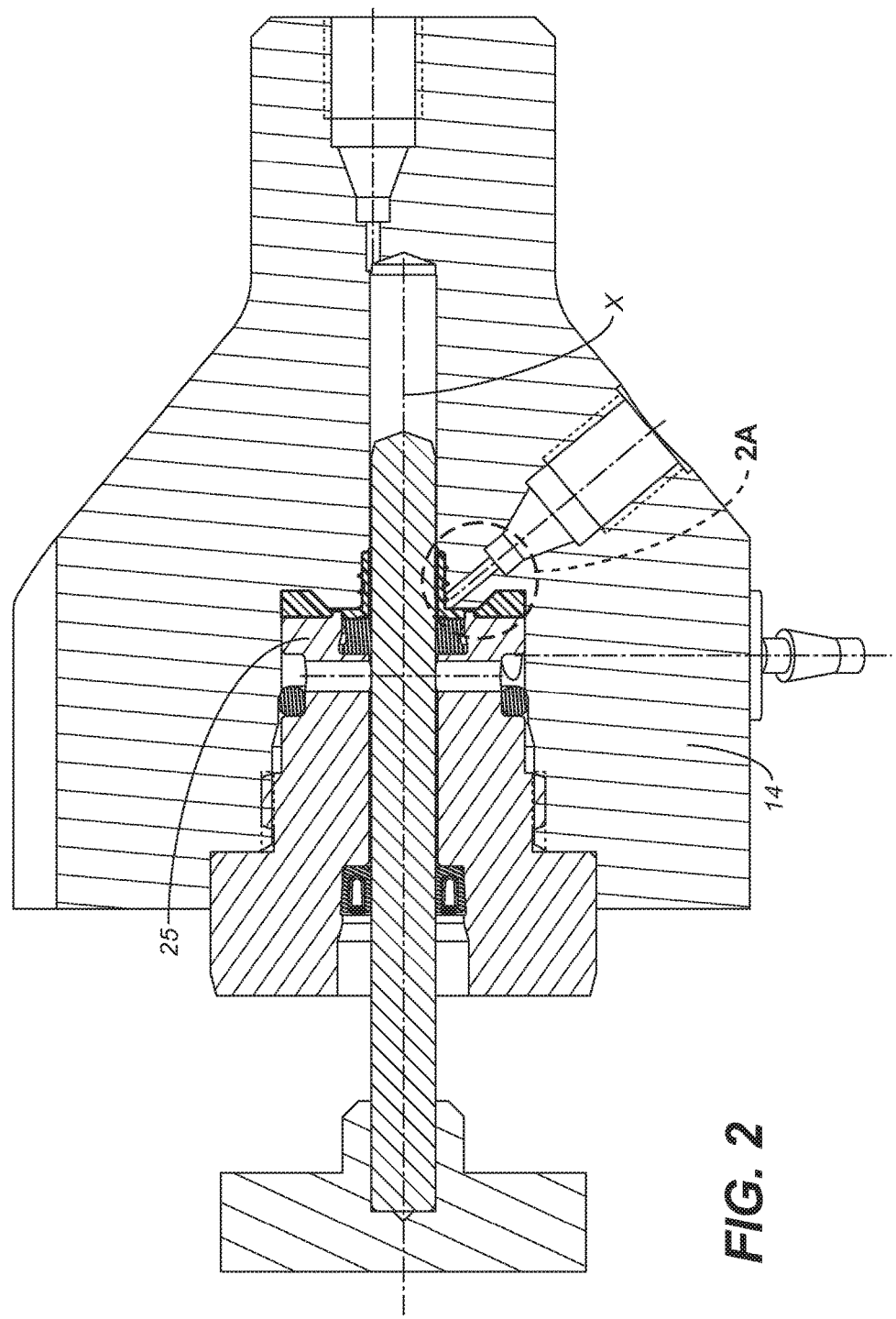
FIG. 2 shows the arrangement according to FIG. 1 after installation of the piston rod.

FIG. 2 shows the arrangement according to FIG. 1 after installation of the piston rod and clamping of the seal into position. The piston rod 11 has been pushed in the X direction on the inner side of the sliding element 21, as a result of which the previously conical or cylindrical sliding element 21 produced with an undersize has been expanded to form a cylindrical shape along the piston wall. The radial prestress inward, introduced as a result into the sliding element 21, produces a first sealing action irrespective of the operating pressure prevailing in the stroke space 40. The sealing portion 24 has also been expanded to form a substantially cylindrical shape by insertion of the piston rod 11. The prestress produced as a result in the first sealing portion 24 acts radially inward on the sliding element 21 and on the piston rod 11 and produces an additional sealing action.

In order to press the seal 30 into the seat 22 thereof, a press-on element 25 is screwed along the X axis into the pump head via suitable screwing means in order with its end side 45 to act upon the seal. The material connection 26 according to FIG. 1 between the first sealing portion 24 and the second sealing portion 20, which is spaced apart radially outward with respect thereto, is subjected to an axial compression force by an annular projection 28 of the press-on element 25 when the seal is clamped into position. By continued screwing of the press-on element 25 in the direction of the seal 30, firstly the annular projection 28 produces the material thin point 26' (illustrated in FIG. 2A) with the acted upon sealing material being displaced radially inward with respect to the first sealing portion 24 (see, e.g., inwardly displaced material 27) and radially outward into the second sealing portion 20. Secondly, according to the invention, such a high pressure is produced in the sealing portion 20 by the press-on element that the material of the sealing portion 20 completely fills the space available thereto between housing 14 and press-on element 25, nestles tightly against the wall surfaces bounding said sealing portion and is elastically compressed. The thin point 26' here is selected to be so narrow in the axial direction that a material passage from the sealing portion 20 in the direction of the sealing portion 24 is suppressed, and therefore the sealing portion 20 is continuously clamped into its seat under high pressure. As a result, a very good static sealing action is obtained along the seat of the sealing portion in the housing 14.

On the inner side of the material thin point 26, when the seal is pressed into position, the first sealing portion 24 is also pressurized, with it being possible for the latter to yield to the pressurization by means of deformation since, unlike the static sealing portion 20, the sealing portion 24 is not surrounded or embedded so tightly.

A narrow pressure volume 50 which is connected to the stroke space 40 via a narrow gap between piston rod 11 and wall of the stroke space 40 is formed on the outer side, which faces away from the X axis, of the first sealing portion 24. The pressure prevailing in the stroke space 40 thus also acts on the outer side of the first sealing portion 24 and produces a radially inwardly directed press-on force which, in addition to the prestressing force already mentioned, achieves a particularly good sealing action.

The sealing system according to the invention produces a dynamic sealing action along the contact between piston rod 11 and sliding element 21, and a static sealing action along the contact surface between second sealing portion 20 and housing 14, wherein the static sealing portion 20 can be acted upon with high pressure by the thin point 26' according to the invention as far as the elastic compression while the dynamic sealing portion 24 remains dimensionally stable and is pressed for sealing purposes against the piston rod 11 by radial prestress and/or pressurization from the stroke space 40.

What is claimed is:

1. A sealing system comprising:
a housing, the housing having a pressurizable stroke space in relation to a movable rod, the pressurizable stroke space is formed about an axis;
a press-on element including an annular projection; and
a seal including:
a first dynamic sealing portion configured to encircle the rod and seal between the seal and the rod; and
a second static sealing portion extending radially from the first sealing portion and configured to seal between the seal and the housing,
wherein the first and the second sealing portions are formed integrally with each other of a sealing material, and
wherein the first sealing portion merges into the second sealing portion via a thin portion formed by compression of a portion of the second sealing portion when the press-on element is pressed against the seal mounted on the housing to define a narrow clearance between the annular projection and the housing, wherein the narrow clearance restricts extrusion of the sealing material from the second sealing portion through the narrow clearance in the direction of the first sealing portion when pressurized.

2. The sealing system as claimed in claim 1, wherein the second sealing portion is bounded by the thin portion, the housing and a press-on element, and screwing the press-on element onto the housing causes a predetermined pressure in the second sealing portion.

3. The sealing system as claimed in claim 1, wherein the thin portion has a thickness of less than 0.5 mm.

4. The sealing system as claimed in claim 1, wherein the thin portion has a thickness of less than 0.1 mm.

5. The sealing system as claimed in claim 1, wherein the thin portion has a thickness of less than 0.05 mm.

6. The sealing system as claimed in claim 1, wherein the thin portion encircles the axis as a ring.

7. The sealing system as claimed in claim 6, wherein the thin portion includes a rectangular cross section.

8. The sealing system as claimed in claim 3, wherein the thickness of the thin portion is a smallest distance between two opposite boundary lines in a cross section of the thin portion where the two opposite boundary lines extend perpendicularly to the axis.

9. The sealing system as claimed in claim 1, wherein the first sealing portion is configured to extend parallel to a central axis thereof, and includes a portion configured to press against the rod at a pressure prevailing in the stroke space.

10. A sealing system comprising:
a housing, the housing having a pressurizable stroke space in relation to a movable rod, the pressurizable stroke space is formed about an axis;
a seal including a first dynamic sealing portion configured to encircle the rod and seal between the seal and the rod, and a second static sealing portion extending radially from the first sealing portion and configured to seal between the seal and the housing, wherein the first and the second sealing portions are formed integrally with each other of a sealing material; and
a press-on element including an annular projection, the press-on element configured to subject the seal to a press-on force in an axial direction to displace the sealing material of the seal radially in a plastic or elastic manner so that the annular projection produces a thin portion defined by a narrow clearance between the annular projection and the housing, in which the first sealing portion merges into the second sealing portion via the thin portion formed by compression of the second sealing portion by the annual projection against the housing, wherein the narrow clearance between the annular projection and the housing restricts extrusion of the sealing material from the second sealing portion through the narrow clearance in the direction of the first sealing portion when pressurized.

11. The sealing system of claim 10 further comprising: a sliding element configured to be pressed into a region of the first sealing portion to form a form-fitting connection in the axial direction between the first sealing portion and the sliding element.

12. The sealing system as claimed in claim 10, wherein the thin portion has a thickness of less than 0.5 mm.

13. The sealing system as claimed in claim 10, wherein the thin portion is formed as a ring and includes a rectangular cross section.

14. The sealing system as claimed in claim 13, wherein a thickness of the thin portion is a smallest distance between two opposite boundary lines in a cross section of the thin portion where the two opposite boundary lines extend parallel to one another.

15. A sealing system comprising:
a rod movable along an axis;
a housing including a seal seat and a pressurizable stroke space extending along the axis from the seal seat, the rod extending into the stroke space;
a seal received by the seal seat, the seal including a first dynamic sealing portion extending along the axis and encircling the rod to seal between the seal and the rod, and a second static sealing portion extending radially from one end of the first sealing portion and configured to seal between the seal and the housing, wherein the first and the second sealing portions are integrally formed of a sealing material; and
a press-on element screwed into the housing along the axis, the press-on element including an annular projection subjecting a press-on force against the second sealing portion as the press-on element is screwed into the housing, the annular projection compressing a portion of the second sealing portion against the seal seat to form a thin portion in the second sealing portion defined by a narrow clearance between the annular projection and the seal seat;
wherein the narrow clearance between the annular projection and the seal seat restricts extrusion of the sealing material from the second sealing portion through the narrow clearance in the direction of the first sealing portion when pressurized.

16. The sealing system of claim 15, wherein the thin portion has a rectangular cross section having a thickness of less than 0.5 mm.

17. The sealing system of claim 15, wherein another end of the first sealing portion includes an outer circumference in fluid communication with the stroke space, wherein the prevailing pressure of the stroke space acts on the outer circumference to radially force the first sealing portion inwardly against the rod.

18. The sealing system of claim 15, wherein the first sealing portion includes a sliding element radially prestressed inwardly against the rod.

19. The sealing system of claim 18, wherein the first sealing portion includes a tapered portion that produces a prestressing force against the sliding element.

* * * * *